United States Patent [19]

Smith et al.

[11] Patent Number: 5,237,097
[45] Date of Patent: Aug. 17, 1993

[54] CATALYTIC CARBONYLATION PROCESS

[75] Inventors: David W. Smith, Cincinnati; Ronnie M. Hanes, Loveland, both of Ohio

[73] Assignee: Quantum Chemical Corporation, New York, N.Y.

[21] Appl. No.: 994,819

[22] Filed: Dec. 22, 1992

Related U.S. Application Data

[63] Continuation of Ser. No. 477,701, Feb. 9, 1990.

[51] Int. Cl.$^5$ .................... C07C 51/10; C07C 51/12
[52] U.S. Cl. ................... 562/519; 560/232; 560/233; 560/175; 562/517; 562/406
[58] Field of Search ............ 560/233, 232, 175; 562/406, 517, 519

[56] References Cited

U.S. PATENT DOCUMENTS

| | | |
|---|---|---|
| 3,579,552 | 5/1971 | Craddock et al. |
| 3,769,326 | 10/1973 | Paulik et al. |
| 3,769,329 | 11/1973 | Paulik et al. |
| 3,772,156 | 11/1973 | Johnson et al. |
| 3,813,428 | 5/1974 | Paulik et al. |
| 3,818,060 | 6/1974 | Forster et al. |
| 3,845,121 | 10/1974 | Eubanks et al. |
| 3,887,489 | 6/1975 | Fannin et al. |
| 4,433,166 | 2/1984 | Singleton et al. |
| 4,690,912 | 9/1987 | Paulik et al. |
| 5,144,068 | 9/1992 | Smith et al. ............ 562/519 |
| 5,155,261 | 10/1992 | Marston et al. ......... 562/519 |
| 5,169,982 | 12/1992 | Heinz et al. ............ 562/519 X |

Primary Examiner—Arthur C. Prescott
Attorney, Agent, or Firm—Kenneth D. Tremain; Gerald A. Baracka

[57] ABSTRACT

A process is disclosed for the carbonylation of an organic compound selected from the group consisting of an olefin, an alcohol, an acid and an ester. In this process the organic compound is reacted with carbon monoxide in the presence of a Group VIII metal-containing catalyst. The liquid carbonylation product solution of this reaction is conveyed to a separation zone maintained at a lower total pressure than is the pressure in the reaction zone. Simultaneously with the conveyance of the liquid product solution to the separation zone is the introduction therein of a carbon monoxide-containing gaseous stream, the carbon monoxide therein contributing a partial pressure of up to 30 psia of the total pressure in said separation zone. A portion of the liquid carbonylation product solution is flashed and removed from the separation zone. The unflashed liquid carbonylation product solution is recycled back into the reaction zone.

23 Claims, No Drawings

CATALYTIC CARBONYLATION PROCESS

CROSS-REFERENCE TO RELATED APPLICATION

The present application is a continuation of U.S. patent application Ser. No. 477,701 filed Feb. 9, 1990.

BACKGROUND OF THE DISCLOSURE

1. Field of the Invention

Carbonylation of olefins, alcohols, acids and esters represents a very important, commercially developed processing scheme. In this process an olefin, an alcohol, an acid or an ester is contacted with carbon monoxide in the presence of a carbonylation catalyst. Many such catalysts have been disclosed and utilized in the prior art.

Recently, rhodium-containing compounds, preferably rhodium halides such as the iodide and the bromide, have been used in commercially established processes. The advantage of this class of catalysts over earlier catalytic agents utilized in this art is that the extreme thermodynamic conditions required in carbonylation reactions of the prior art are significantly eased. Specifically, the high carbon monoxide partial pressure required in reactions utilizing prior art carbonylation catalysts is decreased. Those skilled in the art are aware of the advantages obtained when the pressure of a reaction is decreased.

Although the utilization of these recently developed catalyst systems have significantly advanced the carbonylation art, this catalyst system is subject to an important failing. That failing relates to the fact that rhodium halides are homogeneous in the carbonylation reaction mixture and thus separation of the carbonylation product from the liquid reaction mixture containing the homogeneous catalyst is difficult. As a result, the removal of the product results in the removal of catalyst included therewith. In view of the high cost of catalyst, this failing results in significantly higher processing costs than would be the case if the catalyst could be separated from the product.

To overcome this critical deficiency proposals have been advanced wherein at least a portion of the liquid reaction mass is transferred from the reactor to a separation zone of substantially lower pressure. Therein, in the absence of heat, a portion of the carbonylation product is flashed. The unvaporized liquid carbonylation reaction mixture remaining, including the homogeneous catalyst, is recycled back into the reactor zone. With this scheme the advantages of a homogeneous catalyst system are obtained while overcoming its attendant separation problem.

While this advance in the art represents an improvement over prior art processes utilizing rhodium-containing catalysts, it still is subject to an important failing. That is, during the separation step the soluble rhodium-containing homogeneous catalyst is subject to precipitation. Those skilled in the art are aware of the criticality of this effect. Although the use of a processing scheme which includes a separation zone eliminates the loss of catalyst dissolved in the removed product, it substitutes a similar failing, the loss of high cost rhodium-containing catalyst by precipitation. An amount of soluble rhodium-containing compound catalyst, equal to that lost to precipitation in the separation zone, must thus be added to the unflashed liquid therein.

To overcome this serious deficiency a process has been developed wherein tin or a tin-containing compound is added to the carbonylation product mixture in the separation zone. The addition of tin or a tin compound has the effect of maintaining the rhodium compound catalyst in solution. Although the introduction of tin or a tin compound maintains the rhodium catalyst in solution, and thus eliminates the problem associated with rhodium precipitation, it creates still another problem. Those skilled in the art are aware that tin or a tin-containing compound is highly reactive. It reacts with the halogen component present in the catalyst to produce tin halide salts. These tin halide salts oftentimes evaporate under the aforementioned flashing conditions and are carried downstream where they contact metallic processing equipment. Since tin halide salts are corrosive, they create a major corrosion problem in the processing equipment utilized in the carbonylation reaction.

The above discussion not only emphasizes the desirability of developing a new processing scheme but also of substituting other equally effective carbonylation catalysts which provide the advantages obtained by the use of rhodium halides without the attendant problems discussed above.

2. Background of the Prior Art

The references relevant to the present invention include those disclosures which describe the developments discussed above. Thus, U.S. Pat. No. 3,579,552 to Craddock et al. discloses a process for the preparation of carboxylic acids by the reaction of ethylenically unsaturated compounds with carbon monoxide and water in the presence of catalyst systems which include rhodium compounds and complexes together with an iodide promoter.

A related development is described in U.S. Pat. No. 3,769,326 to Paulik et al. The '326 patent is similar to the teaching of the aforementioned '552 patent but is specifically directed to the reaction of an aromatic alcohol or ester, ether or halide derivatives thereof. In this process the aromatic species is reacted with carbon monoxide in the presence of a catalyst system containing rhodium and halogen components to produce aromatic carboxylic acids or esters.

U.S. Pat. No. 3,769,329 to Paulik et al. differs from the '326 patent in that the identity of the reactant carbonylated to produce a carboxylic acid or ester is, rather than an aromatic alcohol or derivative thereof, a saturated alcohol, a saturated ether, a saturated ester or a saturated halide. This process includes the proviso that if the reactant is other than an alcohol, water is also present.

A process for purifying carboxylic acid streams, particularly acetic acid streams, synthesized in a carbonylation process which involves the reaction of an alcohol or derivative thereof with carbon monoxide, is taught in U.S. Pat. No. 3,772,156 to Johnson et al. In this process hydrogen iodide or an alkyl iodide is employed as a catalyst promotor. The removal of iodine, which is thus present as an impurity, is the inventive feature of the '156 patent. In this process an alkali metal compound, an alkaline earth metal compound or a mixture of the two is added to the acid stream to be purified. Hypophosphorous acid is also added to the acid stream if free iodine is present as the contaminant.

A process for production of monocarboxylic acids is set forth in U.S. Pat. No. 3,813,428 to Paulik et al. In this process an alcohol having the formula R-CH$_2$OH, where R is phenyl or hydroxymethyl, is reacted with carbon monoxide in the presence of a catalyst system comprising rhodium or iridium compounds and complexes, together with a halide promoter. This process is applicable also to halide, ester or ether derivatives of the alcohol.

U.S. Pat. No. 3,818,060 to Forster et al. describes a carboxylation process resulting in the synthesis of a carboxylic acid. In this process an ethylenically unsaturated compound is reacted, in the liquid phase, with carbon monoxide and water in the presence of a catalyst system comprising a rhodium or iridium compound, a halide promoter and, as a stabilizer, an organic derivative of pentavalent phosphorous, arsenic, antimony, nitrogen or bismuth.

U.S. Pat. No. 3,845,121 to Eubanks et al. discloses a process for separating carbonylation products from a carbonylation product mixture. In this process an olefin, an alcohol or an ester, a halide or an ether derivative of said alcohol in the liquid phase is reacted with carbon monoxide in the presence of a catalyst system. The catalyst system contains a rhodium or an iridium component and an iodide or bromide component. This liquid product mixture is passed from the reaction zone to a separation zone of substantially lower pressure, without the addition of heat and in the absence of any additional component such as carbon monoxide gas, wherein a portion of the carbonylation product is vaporized and withdrawn from the separation zone.

U.S. Pat. No. 3,887,489 to Fannin et al. sets forth a method of treating a spent catalyst solution which includes a complex reaction product which includes a rhodium component, a halogen component, carbon monoxide and metallic corrosion products. The treatment includes heating the spent solution under agitation at a temperature of about 100° C. to about 190° C. and a pressure sufficient to boil off the carbon monoxide and precipitate the rhodium component. The precipitated rhodium-containing component is redissolved by adding solvent, either water, acetic acid or a mixture thereof, and a halogen component, preferably iodine, under the accompanying thermodynamic conditions of elevated temperature and pressure, said pressure provided by the partial pressure of carbon monoxide gas. This process results in the reformation of the catalyst solution, that is, the redissolving of the rhodium catalyst in the absence of the corrosion products present in the thus processed spent solution.

U.S. Pat. No. 4,433,166 to Singleton et al. teaches a carbonylation process in which an olefin, an alcohol or an ester, halide or ether derivative of the alcohol is reacted with carbon monoxide in the liquid phase. The reaction occurs in the presence of a catalyst system containing a rhodium component and an iodine or bromine component. The liquid reaction mass incorporating these reactants and catalyst system is passed from the reactor to a separator of substantially lower carbon monoxide partial pressure wherein a portion of the carbonylation product, as well as unreacted gaseous reactants such as carbon monoxide, inert gases and unreacted reactants, is vaporized and withdrawn from the separation zone. The invention of the '166 patent lies in the introduction, into the separator, of tin or a tin compound which acts as a stabilizer to prevent rhodium precipitation.

Yet another relevant reference is U.S. Pat. No. 4,690,912 to Paulik et al. which is directed to a catalyst system for the production of carbonylation products by the reaction of a carbonylatable reactant and carbon monoxide. The catalyst system comprises a rhodium-containing catalyst which includes an adduct of a rhodium-containing component source material and carbon monoxide and a separately added iodine-containing promoter component with the proviso that the promoter contains more iodine atoms than the catalyst contains rhodium atoms.

BRIEF SUMMARY OF THE INVENTION

A new process has now been developed which permits carbonylation of olefins, alcohol, acids and esters wherein the advantages of utilizing a Group VIII metal-containing catalyst are obtained consistent with the complete separation of the carbonylation product from the catalytic agent. This desirable result occurs without the attendant disadvantage noticed in processes of the prior art which utilize Group VIII metal-containing catalysts. That is, in the present process the separation of the carbonylation product from the Group VIII metal catalyst is not accompanied by precipitation of the Group VIII metal catalyst.

In accordance with the present invention a process for carbonylating an olefin, an alcohol, an carboxylic acid or a carboxylic acid ester is disclosed. In this process an olefin, an alcohol, an acid or an ester is reacted, in a carbonylation reaction zone, with carbon monoxide in the presence of a Group VIII metal-containing catalyst at elevated pressure wherein a liquid carbonylation product solution is obtained. The liquid carbonylation product solution is conveyed to a separation zone of lower pressure simultaneously with the introduction therein of a carbon monoxide-containing gas stream which comprises carbon monoxide maintained at a partial pressure of up to about 30 psia wherein a portion of the liquid carbonylation product solution is flashed off in the gaseous state. The fraction of the liquid carbonylation product solution not flashed off and removed is recycled to the carbonylation reaction zone.

DETAILED DESCRIPTION

The process of the present invention involves an improvement in the carbonylation of an organic compound selected from the group consisting of a olefin, an alcohol, an acid and an ester. In this carbonylation process a reactant, selected from one of these classes of organic compounds, all in the liquid phase, is catalytically reacted with carbon monoxide at elevated pressure in a carbonylation reaction zone. The liquid carbonylation reaction product solution formed in the reaction zone is conveyed to a separation zone, a zone of lower pressure compared to that of the reaction zone. Therein, under the thermodynamic conditions present in the separation zone, a significant fraction of the liquid carbonylation reaction product solution conveyed therein from the reaction zone is flashed. Significantly, in the process of the present invention, a homogeneous catalytic agent, present in the liquid carbonylation product solution, remains in solution and is recycled back, along with the portion of the liquid carbonylation product solution which is unflashed, into the reaction zone. In this manner the problems associated with this carbonylation reaction in the prior art is overcome. It is noted that the flashed off product is transferred to a purification zone to separate the desired carbonylation product from undesired side products.

Among the organic compound reactants within the contemplation of this invention are olefins. Olefins preferred for use in this process include those having 2 to 4 carbon atoms. Thus, preferred olefin reactants in this carbonylation process include ethylene, propylene, n-butene, and 2-methylpropene.

Another preferred class of reactants are alcohols. Of the alcohols preferred for use in this carbonylation reaction, alkanols containing 1 to 4 carbon atoms are preferred. Therefore, such alkanols as methanol, ethanol, n-propanol, isopropanol, n-butyl alcohol, sec-butyl alcohol and t-butyl alcohol are preferred for use.

A third preferred class of reactants are esters. Esters within the contemplation of the carbonylation process of the subject invention include methyl acetate, ethyl acetate, propyl acetate, methyl propionate, ethyl propionate, propyl propionate and the like. Of these preferred esters, methyl acetate is particularly preferred. These esters are generically defined as $C_1$–$C_4$ alkyl $C_2$–$C_6$ alkanoates. This generic class of esters are thus preferred for use in the present invention.

Of the three above-discussed more preferred classes of reactants within the contemplation of this invention, the alcohols are most preferred. Of the preferred alkanols within the generic class of alcohols within the contemplation of this invention, methanol and ethanol are particularly preferred, with methanol being most preferred. In that the use of methanol in the process of the present invention is most preferred, it should be emphasized that liquid carbonylation product solution synthesized when the reactant is methanol includes acetic acid.

A catalytic agent is charged into the reaction zone with the reactants in the present carbonylation process. The catalytic agent is characterized by the inclusion therein of a Group VIII metal. Of the Group VIII metals within the contemplation of the Group VIII metal-containing catalyst of this invention, rhodium, ruthenium, palladium, cobalt and nickel are preferred. Of these, rhodium, cobalt and nickel are particularly preferred. Of these particularly preferred Group VIII metals, rhodium is most preferred.

The Group VIII metal may be present in the catalyst in elemental form, as a salt thereof, as an oxide thereof, as an organic compound or as an organic complex. Of these forms, the elemental metal, an oxide thereof, a halide of a Group VIII metal, a nitrate of a Group VIII metal, a Group VIII metal sulfate, a Group VIII metal sulfide, a carbonyl of a Group VIII metal, a carbonyl halide of a Group VIII metal and an acetate of a Group VIII metal are preferred. In that the most preferred Group VIII metal is rhodium, such catalytic agents as rhodium metal, rhodium oxide, an organorhodium compound, a rhodium carbonyl complex, a rhodium carbonyl halide, rhodium nitrate and rhodium halides, i.e., rhodium chloride, rhodium bromide and rhodium iodide are particularly preferred catalytic agents in this carbonylation process. Of these carbonylation catalysts, rhodium metal, rhodium oxide, a rhodium halide and a rhodium carbonyl complex are even more particularly preferred. The rhodium halide, rhodium iodide is the most preferred of these.

In the carbonylation reaction zone of this process the reactants, the organic liquid carbonylatable compound and carbon monoxide gas, are contacted in the presence of the Group VIII metal-containing catalyst at a pressure in the range of between about 15 psia and about 1500 psia. Preferably, the pressure in the reaction zone is in the range of between about 50 psia and about 1000 psia. More preferably, the pressure in the reaction zone is in the range of between about 100 psia and about 750 psia. Still more preferably, the pressure in the reaction zone is in the range of between about 300 psia and about 500 psia. Even more preferably, the pressure of the carbonylation reaction is in the range of between about 380 psia and about 420 psia.

The temperature of the carbonylation reaction, that is, the temperature in the carbonylation reaction zone, ranges between about 50° C. and about 500° C. Preferably, the temperature range in the reaction zone is between about 75° C. and about 275° C. More preferably, the temperature in the reaction zone is in the range of between about 160° C. and about 200° C. Most preferably, the temperature in the reaction zone is between about 180° C. and about 190° C.

The reaction product, a liquid carbonylation product solution formed in the reaction zone at the thermodynamic conditions recited above, is next transmitted to a separation zone. The separation zone is maintained at a pressure considerably lower than the pressure in the carbonylation reaction zone. Those skilled in the thermodynamic arts are aware that this pressure reduction is accompanied by flashing of the more volatile components of the liquid reaction product solution. In this way, the carbonylation product, which has a higher vapor pressure than the catalyst, is removed as a vapor leaving behind the catalytic agent in the unflashed liquid carbonylation product solution. This separation is desirable in that a fraction of the product is removed as a vapor and is separated from the Group VIII metal catalyst which remains in the liquid phase. Thus, not only is there no loss of high cost catalyst, which is recycled back into the reactor, but, in addition, the product is provided in a form free of catalytic contamination.

This desirable result is obtained without an accompanying problem well documented in the prior art. In many prior art processes precipitation of the catalytic agent occurs in the separation zone. This problem is overcome in the unique process of the present invention by introducing a carbon monoxide-containing gaseous stream into the separation zone along with the liquid carbonylation product solution which enters the separation zone from the carbonylation reaction zone.

The carbon monoxide gas introduced into the separation zone contributes a partial pressure of up to 30 psia. Preferably, carbon monoxide gas introduced into the separation zone in the carbon monoxide-containing gaseous stream provides a partial pressure in the range of between about 2 psia and about 30 psia. More preferably, the partial pressure contributed by the carbon monoxide gas introduced into the separation zone is in the range of between about 4 psia and about 28 psia. Still more preferably, the partial pressure of the carbon monoxide gas introduced into the separation zone is in the range of between about 10 psia and about 26 psia.

The thermodynamic conditions maintained in the separation zone comprises a total pressure, including that provided by the partial pressure of the carbon monoxide, in the range of between about 15 psia and about 60 psia. Preferably, the separation zone total pressure is in the range of between about 15 psia and about 45 psia. More preferably, the total pressure in the separation zone is maintained at between about 20 psia and about 40 psia. Still more preferably, the total pressure in the separation is in the range of between about 20 psia and about 25 psia. The temperature in the separation zone is in the range of between about 100° C. and about 150° C. Preferably, the temperature is in the range of between about 120° C. and about 140° C. Still more preferably, the temperature in the separation zone is in the range of between about 125° C. and about 135° C.

The carbon monoxide-containing gaseous stream introduced into the separation zone encompasses any gaseous mixture which includes carbon monoxide contributing a finite partial pressure of up to 30 psia. Preferably, the partial pressure contributed by the carbon monoxide gas introduced into the separation zone is in the range of between about 2 psia and about 30 psia. More preferably, the carbon monoxide separation zone partial pressure is in the range of about 4 psia to about 28 psia. Still more preferably, the carbon monoxide provides a partial pressure, in said separation zone, of between about 10 psia and about 26 psia.

In a preferred embodiment of the carbon monoxide-containing gaseous stream introduced into the separation zone the stream comprises a gaseous mixture including carbon monoxide present in a concentration of more than 50% by volume. A preferred gaseous mixture includes carbon dioxide, methane, nitrogen and hydrogen, as well as the aforementioned carbon monoxide present in a concentration of more than 50% by volume. In another preferred embodiment of the carbon monoxide-containing gaseous stream, the gas stream is pure carbon monoxide. That is, the stream is neat carbon monoxide.

Independent of the source of carbon monoxide, whether it is supplied neat or as part of a gaseous mixture, one preferred embodiment includes the feeding of the carbon monoxide-containing gaseous stream into the liquid phase of the contents of the separation zone. That is, the gaseous stream is bubbled through the liquid carbonylation product solution. This method, involving intimate contact of liquid and gas, improves retention of the Group VIII metal catalyst in the unflashed liquid that is recycled back into the reaction zone.

The following examples are given to illustrate the scope of the present invention. Because these examples are given for illustrative purposes only, the scope of the present invention should not be limited thereto.

EXAMPLE 1

A solution typical of those obtained in the carbonylation of methanol with carbon monoxide was prepared. The solution had the following constituency: 114 ml. acetic acid, 21.4 ml. water, 1.5 ml. 47% aqueous solution of hydrogen iodide, 0.12 ml. methyl iodide, 0.4 ml. methyl acetate and 0.56 g. rhodium iodide. This solution was initially exposed to carbon monoxide maintained at a pressure of 400 psia and a temperature of 185° C. The solution was thereafter cooled, connected to a source of 25 psia carbon monoxide and then immersed in a 125° C. oil bath.

Three samples of the thus processed solution were disposed in 3 oz. thick walled pyrex glass tubes. Each tube was charged with a sample of the above-recited solution. Specimens of the samples connected to said 25 psia CO and immersed in the 125° C. oil bath were removed and centrifuged after 4 hours and 24 hours.

Each of the supernatant liquid specimens were analyzed by atomic absorption to determine the soluble rhodium concentration in the sample. From this determination the percent rhodium lost in each of the three samples was calculated. The average of these three results is reported in the Table.

COMPARATIVE EXAMPLE 1

Two additional samples of the carbonylation product solution having the constituency reported in Example 1 were prepared. The two samples, like those in Example 1, were disposed in communication with a reservoir of carbon monoxide maintained at a pressure of 400 psia at a temperature of 185° C. The samples were then cooled. After cooling the samples were poured into two 3-ounce glass tubes, identical to the tubes utilized in Example 1. The samples in the tubes were next purged with nitrogen. Like the procedure of Example 1, the samples were then placed in an oil bath maintained at a temperature of 125° C. Unlike the procedure of Example 1, the samples were not connected to a source of carbon monoxide. The autogenous pressure of the sample constituents was about 30 psia.

As in Example 1 specimens of the samples were taken after 4 and 24 hours. These samples were analyzed for their rhodium content, employing atomic absorption techniques. Rhodium loss was thus calculated for each of the samples. Average rhodium loss, based on the average of the losses in the two samples, appears in the Table.

EXAMPLE 2

The procedure of Example 1 was repeated utilizing the same typical carbonylation product solution employed in that example. The only distinctions between the present example and Example 1 was, first, that only two, rather than three samples, were tested and, second, the carbon monoxide partial pressure in communication with the two samples in the 125° C. oil bath was 20 psia, rather than the 25 psia pressure of Example 1.

The results of this example appear in the Table.

COMPARATIVE EXAMPLE 2

Two additional samples having the same constituency as the liquid carbonylation product solution of Example 1 were processed in accordance with the procedure of Comparative Example 1. Thus, the autogenous pressure in the samples was 30 psia.

The results of this comparative example are summarized in the Table.

TABLE

| Example No. | CO Partial Pres., psia. | Total Pres., psia. | Rhodium Lost, % | |
|---|---|---|---|---|
| | | | After 4 hrs. | After 24 hrs. |
| 1 | 25 | 25 | 3 | 26 |
| CE1 | 0 | 30 | 30 | 95 |
| 2 | 20 | 20 | 9 | 73 |
| CE2 | 0 | 30 | 24 | 88 |

COMPARATIVE EXAMPLE 3

A carbonylation product solution was prepared from the identical components used in the formation of the solution of Example 1. To that end 114 ml. acetic acid, 21.4 ml. water, 1.5 ml. 47% aqueous solution of hydrogen iodide, 0.12 ml. methyl iodide and 0.4 ml. methyl acetate were combined in a solution. To this was added 0.56 g. of solid rhodium iodide accompanied by a blanket of carbon monoxide supplied at a pressure of 67 psia. The temperature of the solution was maintained at 150° C.

The solution of the thus processed components was analyzed by atomic absorption to determine the rhodium concentration in the resultant solution. It was determined that the liquid solution included 140 ppm of rhodium. This represented the dissolving of 19% of the solid rhodium iodide charged into the reactor, in that theoretical calculations establish that if all the rhodium iodide charged into the reactor had dissolved into solution the solution would have included 740 ppm rhodium.

DISCUSSION OF COMPARATIVE EXAMPLE 3

Comparative Example 3 was conducted to establish the non-relevance of the disclosure of dissolving a rhodium or other Group VIII metal compound in a carbonylation solution upon the present invention. The present invention permits the practicing of a continuous process by removing the carbonylation product and retaining the rhodium catalyst in solution in a separation zone, a zone of lower pressure than the pressure in the carbonylation reactor, without the attendant problem associated with such a scheme, the precipitation, in the separation zone, of the rhodium or other Group VIII metal compound. The thus retained rhodium catalyst in solution is recycled back into the carbonylation reactor permitting continuous operation.

The disclosure of a process which teaches the dissolving of a rhodium or other Group VIII metal compound in a carbonylation solution, such as that set forth in the aforementioned Fannin et al. patent, requires high pressure. Fannin et al. specifically necessitates the presence of carbon monoxide at a pressure of 80 psig (95 psia) to dissolve rhodium iodide in a carbonylation solution maintained at 150° C. The present invention, on the other hand, requires the presence of carbon monoxide at a pressure as low as about 2 psia to overcome the well known problem in carbonylation processes of rhodium precipitation during carbonylation product removal.

This advance is based on the identification, in the present invention, of the exact problem, the preventing rhodium precipitation, a problem unassociated with prior art teachings, such as that described by Fannin et al., of dissolving rhodium in carbonylation product solutions.

Comparative Example 3 substantiates the above remarks. Unlike Example 1, wherein a carbonylation solution already containing dissolved rhodium is contacted with carbon monoxide at a pressure of 25 psia, in Comparative Example 3 the same solution, containing no dissolved rhodium iodide, was formed. In accordance with the teaching of Fannin et al. rhodium iodide was added to the thus formed solution. This step was accompanied by the simultaneous introduction of carbon monoxide gas at 67 psia, a higher pressure than the maximum partial pressure, about 30 psia, within the contemplation of the present invention. This higher pressure was required by the autogenous pressure of the solution at 150° C.

As indicated in Comparative Example 3, the portion of the rhodium iodide that dissolved in the solution was such that 140 ppm of rhodium was present therein. Thus, the bulk of the solid rhodium iodide charged into the solution remained undissolved. If all the solid rhodium iodide charged into the solution, 0.56 gram, was dissolved the rhodium concentration in the solution would have been 740 ppm. Therefore, the 140 ppm concentration of rhodium in solution represented the dissolution of only 19% of the rhodium iodide charged into the carbonylation product solution.

The above remarks establish that the teaching of Fannin et al., which requires high pressure, does not produce a result equivalent to the process of the present invention. Whereas Fannin et al. requires very high pressure, i.e., 95 psia, to dissolve a rhodium salt, the process of the present invention necessitates a minimum carbon monoxide partial pressure of 2 psia to successfully prevent rhodium precipitation. That is, Comparative Example 3 establishes, by comparison of the pressures required to successfully maintain a rhodium salt in a carbonylation product solution which includes dissolved rhodium, the non-relevance of Fannin et al.

That Fannin et al. teaches the complete solution of rhodium iodide at 95 psia in a carbonylation solution maintained at 150° C. Comparative Example 3 establishes that dropping that pressure to 67 psia, a reduction of 29%, reduces rhodium dissolution by 81%. This, furthermore, establishes the criticality of employing carbon monoxide at high pressure in the Fannin et al. process.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. In a carbonylation process which includes reacting an organic compound, said organic compound selected from the group consisting of an olefin, an alcohol, an acid and an ester, with carbon monoxide in the presence of a dissolved rhodium-containing catalyst in a reaction zone maintained at a pressure in the range of between about 100 psia and about 750 psia and at a temperature in the range of between about 75° C. and about 275° C., wherein a liquid carbonylation product solution is obtained; conveying said liquid carbonylation solution to a separation zone, said separation zone maintained at a total pressure of between about 15 psia and about 45 psia and at a temperature of between about 100° C. and about 150° C., with the proviso that the total pressure and temperature in said separation zone is lower than in said reaction zone, whereby a fraction of said liquid carbonylation product flashed off from said carbonylation product solution; and recycling the unflashed off liquid carbonylation product solution into said reaction zone, the improvement which comprises feeding carbon monoxide gas, at a pressure of between about 2 psia and about 30 psia and a temperature of between about 100° C. and about 150° C., into said separation zone simultaneously with said carbonylation product solution whereby said rhodium-containing catalyst is not precipitated from said carbonylation product solution in said separation zone.

2. A process in accordance with claim 1 wherein said organic compound is a $C_2$-$C_4$ olefin.

3. A process in accordance with claim 2 wherein said $C_2$-$C_4$ olefin is ethylene.

4. A process in accordance with claim 1 wherein said organic compound is a $C_1$-$C_4$ alkanol.

5. A process in accordance with claim 4 wherein said $C_1$-$C_4$ alkanol is methanol.

6. A process in accordance with claim 1 wherein said organic compound is $C_1$-$C_4$ alkyl $C_2$-$C_6$ alkanoate.

7. A process in accordance with claim 7 wherein said $C_1$-$C_4$ alkyl $C_2$-$C_6$ alkanoate is methyl acetate.

8. A process in accordance with claim 1 wherein said reaction zone is maintained at a pressure in the range of between about 300 psia and about 500 psia and at a temperature in the range of between about 160° C. and about 200° C.

9. A process in accordance with claim 8 wherein said reaction zone is maintained at a pressure in the range of between about 380 psia and about 420 psia and at a temperature in the range of between about 180° C. and about 190° C.

10. A process in accordance with claim 1 wherein said separation zone is maintained at a pressure in the range of between about 20 psia and about 40 psia and at a temperature in the range of between about 120° C. and about 140° C.

11. A process in accordance with claim 10 wherein said separation zone is maintained at a pressure in the range of between about 20 psia and about 25 psia and at a temperature in the range of between of between about 125° C. and about 135° C.

12. A process in accordance with claim 1 wherein said carbon monoxide gas introduced into said separation zone contributes a partial pressure of between about 4 psia and about 28 psia.

13. A process in accordance with claim 12 wherein said carbon monoxide gas introduced into said separation zone contributes a partial pressure of between about 10 psia and about 26 psia.

14. A process in accordance with claim 1 wherein said carbon monoxide gas is introduced into said separation zone by being bubbled through the liquid carbonylation product solution.

15. A process in accordance with claim 1 wherein said rhodium-containing catalyst is selected from the group consisting of rhodium metal, rhodium oxide, an organorhodium compound, a rhodium carbonyl complex, a rhodium carbonyl halide, rhodium nitrate and a rhodium halide.

16. A process in accordance with claim 15 wherein said rhodium-containing catalyst is selected from the group consisting of rhodium metal, rhodium oxide, a rhodium halide and a rhodium carbonyl complex.

17. A process in accordance with claim 16 wherein said rhodium-containing catalyst is selected from the group consisting of rhodium chloride, rhodium bromide and rhodium iodide.

18. A process in accordance with claim 17 wherein said rhodium-containing catalyst is rhodium iodide.

19. In a carbonylation process which includes reacting an alcohol with carbon monoxide in the presence of dissolved rhodium halide in a reaction zone maintained at a pressure in the range of between about 100 psia and about 750 psia and at a temperature in the range of between about 75° C. and about 275° C., wherein a liquid carbonylation product solution is obtained; conveying said liquid carbonylation product solution to a separation zone, said separation zone maintained at a total pressure of between about 15 psia and about 45 psia and a temperature of between about 100° C. and about 150° C., with the proviso that the total pressure and temperature in said separation zone is lower than in said reaction zone, whereby a fraction of said liquid carbonylation product is flashed off from said carbonylation product solution; and recycling said unflashed off liquid carbonylation product solution into said reaction zone, the improvement which comprises feeding carbon monoxide gas, at a pressure of between about 2 psia and about 30 psia and a temperature of between about 100° C. and about 150° C., into said separation zone simultaneously with said carbonylation product solution whereby said rhodium halide is not precipitated from said carbonylation product solution in said separation zone.

20. A process in accordance with claim 19 wherein said reaction zone is maintained at a pressure in the range of between about 300 psia and about 500 psia and at a temperature in the range of between about 160° C. and about 200° C.; said separation zone is maintained at a total pressure in the range of between about 20 psia and about 40 psia and at a temperature in the range of between about 120° C. and about 140° C.; and said carbon monoxide gas introduced into said separation zone contributes a partial pressure of between about 4 psia and about 28 psia.

21. A process in accordance with claim 20 wherein said reaction zone is maintained at a pressure in the range of between about 380 psia and about 420 psia and at a temperature in the range of between about 180° C. and about 190° C.; said separation zone is maintained at a total pressure in the range of between about 20 psia and about 25 psia and a temperature in the range of between about 125° C. and about 135° C.; and said carbon monoxide gas introduced into said separation zone contributes a partial pressure of between about 10 psia and about 26 psia.

22. A process in accordance with claim 21 wherein said rhodium halide is rhodium iodide.

23. A process in accordance with claim 22 wherein said alcohol is methanol.

* * * * *